(12) United States Patent
Emir-Farinas

(10) Patent No.: US 10,335,092 B1
(45) Date of Patent: Jul. 2, 2019

(54) BUILDING PREDICTED FUTURE MEDICAL PROFILES

(71) Applicant: Pivotal Software, Inc., Palo Alto, CA (US)

(72) Inventor: Hulya Emir-Farinas, San Francisco, CA (US)

(73) Assignee: Pivotal Software, Inc., San Francisco, CA (US)

( * ) Notice: Subject to any disclaimer, the term of this patent is extended or adjusted under 35 U.S.C. 154(b) by 806 days.

(21) Appl. No.: 14/627,232

(22) Filed: Feb. 20, 2015

Related U.S. Application Data

(60) Provisional application No. 61/943,191, filed on Feb. 21, 2014.

(51) Int. Cl.
*A61B 5/00* (2006.01)
*G16H 50/30* (2018.01)
*G16H 50/70* (2018.01)

(52) U.S. Cl.
CPC .......... *A61B 5/7275* (2013.01); *A61B 5/7246* (2013.01); *A61B 5/7264* (2013.01);
(Continued)

(58) Field of Classification Search
CPC ........ G06Q 50/22; G06Q 50/24; G06Q 10/04; G06Q 10/10; G06Q 10/06; G16H 50/20;
(Continued)

(56) References Cited

U.S. PATENT DOCUMENTS

| 5,937,387 A | * | 8/1999 | Summerell | ......... | G06F 19/3456 600/301 |
| 2009/0192394 A1 | * | 7/2009 | Guttag | ............... | A61B 5/02405 600/509 |

(Continued)

OTHER PUBLICATIONS

"Time to CARE: a collaborative engine for practical disease prediction", Darcy Davis, et al., Data Min Knowl Disc (2010) 20:388-415, Nov. 25, 2009 (Year: 2009).*

(Continued)

*Primary Examiner* — Joseph D Burgess
(74) *Attorney, Agent, or Firm* — Fish & Richardson P.C.

(57) ABSTRACT

Methods, systems, and apparatus, including computer programs encoded on computer storage media, for creating a probabilistic healthcare value profile for a patient. One of the methods includes obtaining a current medical history including multiple current characteristics of a first patient having a first current age, obtaining multiple sets of age-correlated characteristics, each set corresponding to a different second patient, determining, for one or more sets of the age-correlated characteristics, that characteristics in at least a threshold portion of the respective age-correlated characteristics match one of the multiple current characteristics of the first patient, and generating a future probabilistic medical profile of the first patient, the future probabilistic medical profile including an aggregation of at least a portion of the age-correlated characteristics in the one or more sets, the aggregation including at least one non-matching age-correlated characteristic that does not match any of the current characteristics of the first patient.

43 Claims, 8 Drawing Sheets

(52) U.S. Cl.
CPC .......... *A61B 5/7282* (2013.01); *G16H 50/30* (2018.01); *G16H 50/70* (2018.01)

(58) Field of Classification Search
CPC ........ G16H 50/70; G16H 50/30; G16H 50/50; G16H 10/60; G16H 10/20; G16H 15/00; G16H 80/00; G16H 20/00; G16H 50/80; G06F 19/24; G06F 19/20; G06F 19/18; G06F 19/00; G06F 19/3431; G06F 19/345; G06F 17/30542; G06F 19/10; G06F 19/322; G06F 19/3443; G06F 2216/03; G06F 19/324; G06F 19/3418; G06F 19/3456; G06F 21/602; G06F 21/6245; G06F 21/6254; G06F 2221/2107
See application file for complete search history.

(56) References Cited

U.S. PATENT DOCUMENTS

2011/0307426 A1* 12/2011 Syed ............... G06F 19/00 706/12
2015/0193583 A1* 7/2015 McNair ............ G06F 19/345 705/2

OTHER PUBLICATIONS

Bradford, et al., "Implicit Budget Deficits: The Case of a Mandated Shift to Community-Rated Health Insurance", Tax Policy and the Economy, vol. 11, MIT, Jan. 1997, pp. 129-168, 41 pages.

Alemayehu, et al., "The Lifetime Distribution of Health Care Costs", Health Services Research 39:3, Jun. 2004, 16 pages.

Meerding, et al., "Demographic and Epidemiological Determinants of Healthcare Costs in Netherlands: Cost of Illness Study", British Medical Journal, vol. 317, Jul. 11, 1998, 5 pages.

Fuchs, Victor R., "Provide, Provide: The Economics of Aging", NBER Working Paper Series, National Bureau of Economic Research, Jul. 1998, 34 pages.

Forget, et al., "Variations in Lifetime Healthcare Costs Across a Population", Healthcare Policy, vol. 4, No. 1, 2008, 20 pages.

"Net Present Value", Wikipedia, downloaded from the Internet on Dec. 23, 2013; URL: http://en.wikipedia.org/wiki/Net_present_value, 7 pages.

Vavrus, et al., "Projected Future Temperature and Precipitation Extremes in Chicago", Journal of Great Lakes Research, 2009, 11 pages.

"Futures Studies", Wikipedia, downloaded from the Internet on Dec. 23, 2013, URL: http://en.wikipedia.org/wiki/Futures_studies, 15 pages.

Cost of the Future Newly Insured Under the Affordable Care Act (ACA), Society of Actuaries, Mar. 2013, 83 pages.

* cited by examiner

| | 602a | 604 | 606 | 608 | 610 | 602b |
|---|---|---|---|---|---|---|
| Patient ID | 2 | 4 | 6 | 8 | 10 | 2 |
| Time | $t_0$ | $t_0$ | $t_0$ | $t_0$ | $t_0$ | $t_{0+5}$ |
| Gender | Male | Male | Male | Male | Male | Male |
| Age | 35 | 40 | 40 | 40 | 40 | 40 |
| Diabetes | 0 | 0 | 0 | 0 | 1 | 0 |
| Hypertension | 1 | 1 | 1 | 1 | 0 | 1 |
| High Cholesterol | 1 | 1 | 0 | 1 | 1 | 1 |
| Hypertensive Heart Condition | 0 | 0 | 0 | 0 | 0 | 0.33 |
| Congestive Heart Failure | 0 | 0 | 0 | 0 | 0 | 0 |
| Asthma | 0 | 0 | 0 | 0 | 0 | 0 |
| Rheumatoid Arthritis | 0 | 0 | 0 | 0 | 0 | 0 |
| Annual HC Cost | $18,000 | $34,000 | $22,000 | $16,000 | $35,000 | $24,000 |

FIG. 6

BUILDING PREDICTED FUTURE MEDICAL PROFILES

BACKGROUND

This specification relates to predicted future medical profiles.

People may seek healthcare for various reasons including a common sickness, e.g., a cold; an injury, e.g., one caused by a car accident; a chronic condition, e.g., diabetes; and preventative medicine. Over the course of a lifetime patients may pay for the healthcare themselves. An insurance company may cover some of the patients' healthcare costs. A government agency may pay for some of the patients' healthcare costs.

SUMMARY

In general, one aspect of the subject matter described in this specification can be embodied in methods that include the actions of obtaining, by one or more computers, a current medical history including multiple current characteristics of a first patient having a first current age, obtaining multiple sets of age-correlated characteristics, each set corresponding to a different second patient, each second patient having a second current age that is greater than the first current age, determining, for one or more sets of the multiple sets of the age-correlated characteristics, that characteristics in at least a threshold portion of the respective age-correlated characteristics match one of the multiple current characteristics of the first patient, and generating a future probabilistic medical profile of the first patient, the future probabilistic medical profile including an aggregation of at least a portion of the age-correlated characteristics in the one or more sets, the aggregation including at least one non-matching age-correlated characteristic that does not match any of the current characteristics of the first patient. Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. In particular, one embodiment may include all the following features in combination. The method may include determining, by the one or more computers, a probability of the non-matching age-correlated characteristic occurring to the first patient at a first future age greater than the first current age, wherein the future probabilistic medical profile includes the probability of the non-matching age-correlated characteristic. The method may include presenting, by the one or more computers, the future probabilistic medical profile, an indication of the non-matching age-correlated characteristic, and the corresponding probability of the non-matching age-correlated characteristic occurring to the first patient. Determining the probability of the non-matching age-correlated characteristics occurring to the first patient may include determining, for each of the multiple sets of age-correlated characteristics that include the non-matching age-correlated characteristic, a respective similarity score that represents a degree of similarity between the corresponding second patient and the first patient, and aggregating the similarity scores to determine the probability of the non-matching age-correlated characteristic occurring to the first patient by the time the first patient reaches the first future age. Determining, for each of the multiple sets of age-correlated characteristics that include the non-matching age-correlated characteristic, the similarity score that represents the degree of similarity between the corresponding second patient and the first patient may include determining a ratio of a first quantity of matching age-correlated characteristics from the respective set of age-correlated characteristics to a second quantity of non-matching age-correlated characteristics from the respective set of age-correlated characteristics, and determining the similarity score using the corresponding ratio.

In some implementations, the method may include determining, by the one or more computers and for each of the second patients, a second medical history including the respective set of age-correlated characteristics, wherein the future probabilistic medical profile of the first patient may include an aggregation of the second medical histories of the second patients from the first current age to a first future age greater than the first current age, and determining an estimated future healthcare value for the first patient using the future probabilistic medical profile and the second medical histories. The future probabilistic medical profile of the first patient may include a set of characteristics of the first patient at a second future age greater than the first current age. Determining the estimated future healthcare value for the first patient using the future probabilistic medical profile and the second medical histories may include determining, for each year from the first current age of the first patient to the second future age of the first patient, an estimated healthcare value.

In some implementations, the method may include determining an initial projected medical profile of the first patient, including a set of predicted future characteristics of the first patient at the first future age, using the current medical history, and determining that each characteristic in at least a second threshold portion of age-correlated characteristics from each of the second medical histories matches a corresponding characteristic in the initial projected medical profile of the first patient for an age range of the first patient and the second patients from the current age to the first future age including determining that each characteristic in at least the threshold portion of the respective age-correlated characteristics matches a corresponding characteristic in at least the portion of the set of predicted future characteristics of the first patient. The method may include determining that each characteristic in at least a second threshold portion of age-correlated characteristics for each of the second medical histories matches a corresponding characteristic in the current medical history of the first patient for a predetermined age range of the second patients and the first patient. The predetermined age range is from a younger age to the current age, and the younger age may include an age three to five years younger than the current age.

In some implementations, the method may include determining a current set of characteristics for the first patient at the current age from the current medical history, determining, for each of the second medical histories, a third set of characteristics for the respective second patient at the current age, and determining that each characteristic in at least a second threshold portion of age-correlated characteristics from each of the third sets of characteristics matches a corresponding characteristics in the current set of characteristics for the first patient. Generating the future probabilistic medical profile of the first patient may include generating the future probabilistic medical profile from a weighted average of probabilities of the age-correlated characteristics occurring to the first patient. Generating the future probabilistic medical profile for the first patient may include generating the future probabilistic medical profile for the first patient that is an aggregation of at least a portion of each of the second medical histories and multiple second future probabilistic medical profiles, each of the second future probabilistic medical profiles corresponding to one of the second patients.

In some implementations, the current characteristics of the current medical history may include one or more of biological statistics for the first patient, a medical diagnosis of the first patient, a record of a medical procedure performed on the first patient, a characterization of a hospital visit of the first patient, a record of a medication for the first patient, or a family history of the first patient. Determining, for one or more sets of the multiple sets of the age-correlated characteristics, that characteristics in at least a threshold portion of the respective age-correlated characteristics match one of the multiple current characteristics of the first patient may include determining that the current characteristics of the first patient identify one or more persistent chronic conditions with which the first patient is diagnosed, and determining, for at least one of the second patients, that the age-correlated characteristics of the respective second patient indicate that the respective second patient was diagnosed with at least all of the persistent chronic conditions with which the first patient is diagnosed. The method may include determining a set of persistent chronic conditions, and grouping two or more of the persistent chronic conditions in a condition category upon determining that each of the two or more of the persistent chronic conditions has a different etiology, anatomic site, or manifestation of a particular persistent chronic condition. The method may include determining, for each of the two or more grouped persistent chronic conditions, a corresponding condition healthcare value, and determining that a difference between each pair of the condition healthcare values is statistically insignificant. The method may include generating a second future probabilistic medical profile of the first patient that includes an aggregation of at least a portion of second age-correlated characteristics of third patients having a third current age greater than an average of the second current ages.

The subject matter described in this specification can be implemented in particular embodiments to realize one or more of the following advantages. In some implementations, a system can generate a future probabilistic medical profile for a particular patient and predicted healthcare costs. An entity, e.g., a healthcare insurance company, may use a lifetime healthcare cost model to inform a patient what the patient's future health cost may be. An entity, e.g., an Accountable Care Organization, can use lifetime value models to inform fee structure or capitation decisions, and/or to help estimate the value of interventions and preventive medicine when making recommendations to the public. Policymakers and government agencies, e.g., legislators or disease control centers can estimate the monetary burden of disease by comparing the lifetime healthcare cost of patients with and without a particular disease.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 6 shows an example table of patient medical profiles.

Like reference numbers and designations in the various drawings indicate like elements.

DETAILED DESCRIPTION

Figure 1:
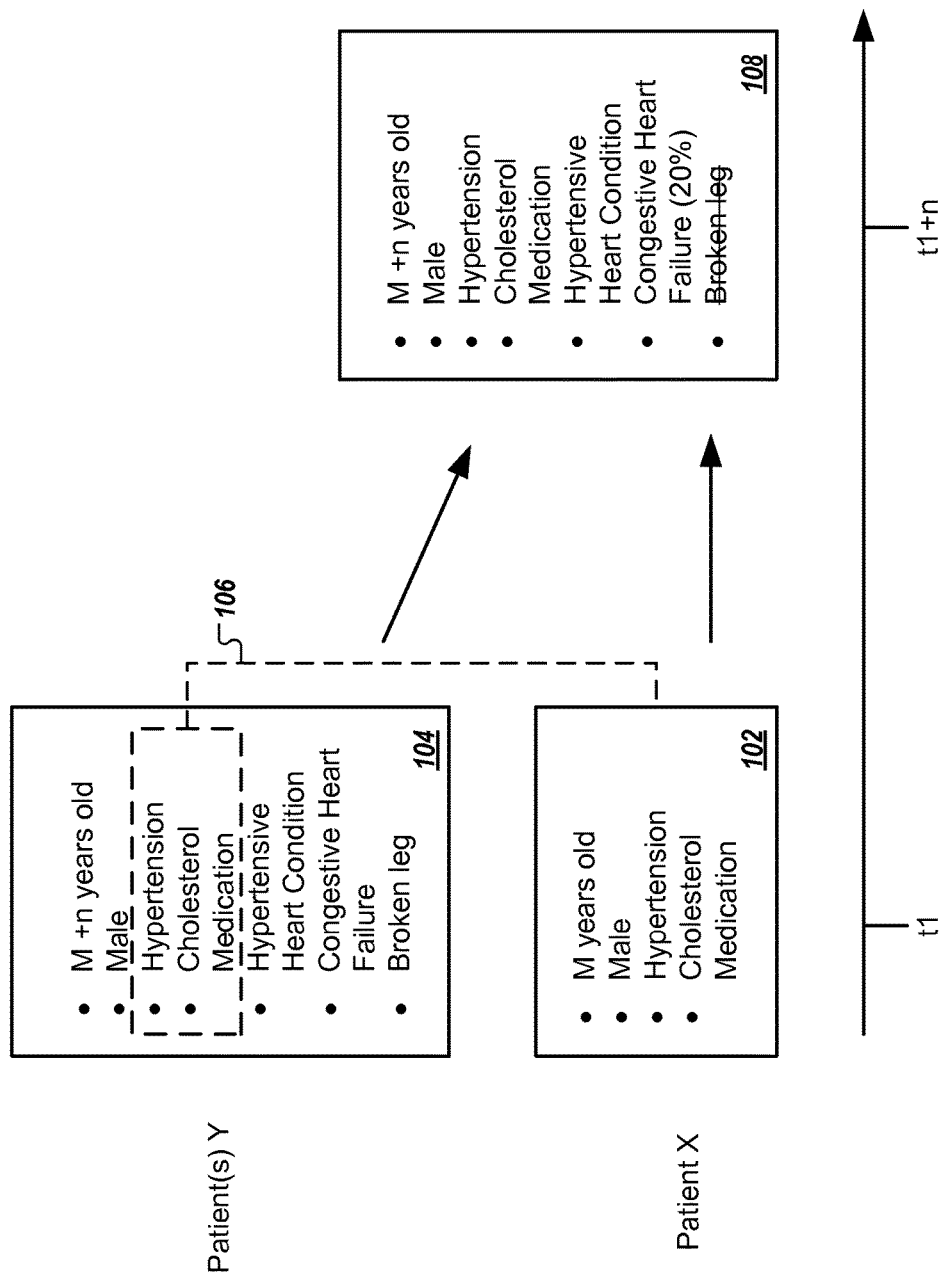
FIG. 1 illustrates techniques for predicting a future medical profile for a patient.

FIG. 1 illustrates techniques for predicting a future medical profile for a patient. At time $t_1$, a medical profile system obtains, from a medical history database, a medical profile 102 for a patient X. The medical profile can include age of patient X at time $t_1$, sex of patient X, and a set of records of medical conditions of patient X up to the time $t_1$. The medical profile system receives a request to predict a medical profile for patent X in the future, e.g., n years later, at time $t_1+n$.

The medical profile system obtains, from the medical history database, medical profiles 104 of one or more patients Y. The medical profile system identifies, from the medical profiles 104, those profiles of patients who have the same sex as patient X and are n year older than patient X. In some implementations, the system identifies a portion of a medical profile 104 of a patient Y who is more than n years older than patient X. The portion includes records in medical profile 104 up to the time that patient Y is n years older than patient X. For example, when, at time $t_1$, patient X is 35 year old, and n=5, a patient Y1 is 50 year old, the system can identify a portion of the medical profile 104 of the patient Y1 up to a time when the patient Y1 is 40 years old.

From those identified profiles or portions of profiles of patients Y, the medical profile system performs a match 106 to determine those medical profiles 104 that similar to the medical profile 102 of patient X. The medical profile system can perform the match 106 by calculating a respective similarity score between each medical profile 104 and the medical profile 102. Details of calculating a similarity score are described below in this specification. The system then selects medical profiles 104 whose similarity scores satisfy a threshold.

From the selected medical profiles 104, the system identifies one or more medical conditions that may or may not be associated with patient X as indicated in the medical profile 102 at time $t_1$. The system can calculate a probability that patient X develops each identified medical condition in the future, at time $t_1+n$. The system can calculate the probability based on the similarity score, a popularity of the medical condition among patients Y, or both. For example, a medical profile 104 includes a record of a condition of congestive heart failure for a patient Y. The system can determine that a higher similarity between this medical profile 104 and the medical profile 102 indicates that patient X will have a higher probability to develop congestive heart failure at time $t_1+n$. Alternatively or additionally, the system can determine that more medical profiles 104 including record of hypertensive heart conditions indicates a higher probability that patient X will develop hypertensive heart condition at time $t_1+n$.

In identifying the one or more medical conditions from the selected medical profiles 104, the system can filter out medical conditions that are pre-classified as one-off conditions. These one-off conditions can include, for example, a broken bone due to an accident, neck injury caused by being hit by a car, and so on. In the example shown, the system filters out a medical condition "broken leg" that has been designed as a one-off condition.

The system then aggregates the identified one or more medical condition by entering these conditions, and optionally, associated probabilities that patient X will develop each of these conditions, into a new medical profile. The system designates the new medical profile as a predicted future medical profile 108 of patient X.

In addition, the system can calculate a predicted medical value, e.g., cost, of patient X at time $t_1+n$. The predicted medical cost can be a per annum cost. The system calculates the predicted medical cost using data from a healthcare cost database. The data includes historical costs of treating the medical conditions that are recorded in the future medical profile 108. For example, the data in the healthcare cost database can indicate treating a given medical condition has a cost of $1,000 for an initial treatment and an annual cost of $200 after the initial treatment, on average, for each patient Y. The system then adds the cost as a component of the predicted medical cost for patient X at time $t_1+n$. The system can adjust the cost for inflation and other factors, e.g., reduction in cost as a result of development of medical technology. The system then adds the respective cost of treating each medical condition, weighted by the respective probability that patient X will develop the condition at time $t_1+n$. The system designates the resulting sum as the predicted medical cost at time $t_1+n$. The system can designate the predicted medical cost as part of future medical profile 108, or as a data item separate from the future medical profile 108. The system can store the future medical profile 108 and the predicted medical cost in a future profile database.

Figure 2:
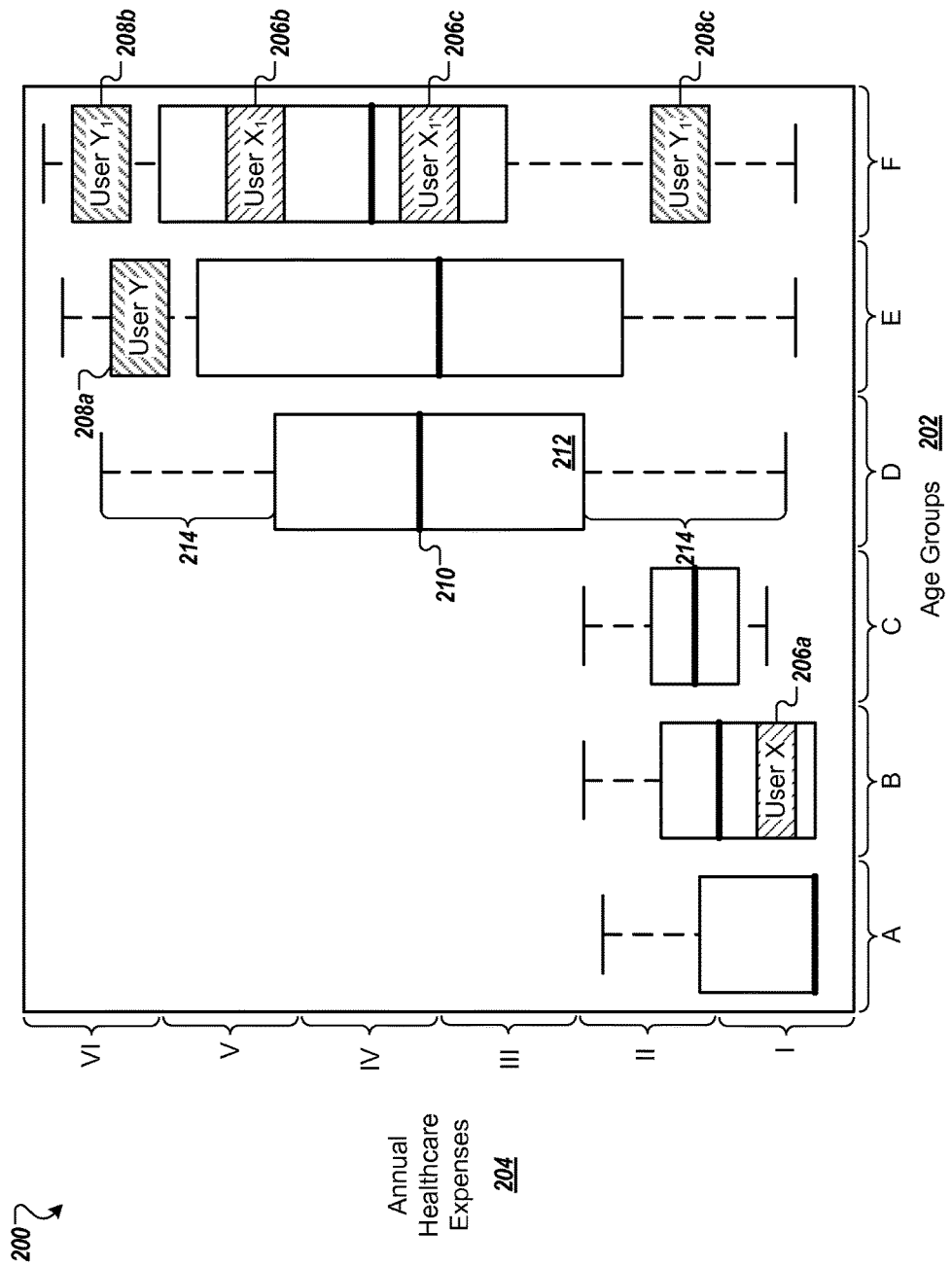
FIG. 2 is an example box plot chart of different patient age groups and per capita annual healthcare expenses for those age groups.

FIG. 2 is an illustrative box plot chart 200 of different patient age groups 202 and per capita annual healthcare expenses 204 for those age groups. A medical profile system determining a possible medical profile for a patient may face multiple challenges. For example, it is sometimes harder for the medical profile system to determine a possible medical profile for a patient, e.g., User X, in ten or more years, e.g., from an age group B to the age group F than a possible medical profile for a patient, e.g., User Y, in three to five years, e.g., from an age group E to an age group F, using solely the patient's own medical history. For example, the medical profile system may be able to determine that the user Y's current costs 208a indicate that the user Y is likely to have particular future costs 208b, rather than future costs 208c, but may be unable to determine whether the User X is likely to have higher future costs 206b or lower future costs 206c based on the user X's current costs 206a and medical history. In addition, high past medical expenses may not be indicative of high future medical expenses, e.g., when a patient has fertility treatment.

The medical profile system may use a patient's current medical history to determine a first estimated future medical profile, e.g., for a short period of time. The medical profile system may use the first estimated future medical profile to identify multiple other patients that have characteristics the same as or similar to the characteristics in the first estimated future medical profile. The medical profile system may also determine that each of the multiple other patients have characteristics that are the same as or similar to characteristics of the patient's current medical history.

The medical profile system may then use the characteristics of the other patients, including estimated future medical profiles for the other patients, to generate a second estimated future medical profile for the patient, e.g., for a longer period of time, such as ten to twenty years. For example, the medical profile system may weight each of the other patients' medical characteristics, e.g., using a degree of similarity between the respective other patient and the patient, and aggregate the weighted medical characteristics together to determine the second estimated future medical profile for the patient.

The medical profile system may then present the second estimated future medical profile to a user, analyze the second estimated future medical profile to determine an estimated healthcare cost or an annual estimated healthcare cost for the patient, or determine potential preventative measures that the patient may take to reduce the likelihood of predicted future medical characteristics.

The age groups 202 A-F represent predetermined ages of users, e.g., 0-10 for the age group A, 11-20 for the age group B, and so on. In another example, the age group A may be from 0-15, the age group B may be from 16-30, and so on.

The annual healthcare expense groups 204 I-VI represent example costs for a patient, e.g., $0-2000 for expense group I, $2001-3000 for expense group II, etc. The size of the annual healthcare expenses groups 204 may increase exponentially, e.g., $0-2000 for expense group I, $2001-6000 for expense group II, and so on.

For each age group, e.g., the age group D, the graph includes a median annual healthcare cost 210, an average healthcare cost range e.g., a range 212 from second to third quartiles, and a potential extended healthcare cost range 214 e.g., the first and last quartiles. The average healthcare cost range 212 represents the annual healthcare costs of a predetermined percentage of patients for the corresponding age group. For example, the average healthcare cost range 212 may represent the healthcare costs of X % of patients in the age group D. The potential extended healthcare cost range 214 represents the annual healthcare costs of a second predetermined percentage of patients for the corresponding age group. For example, the combination of the average healthcare cost range 212 and the potential extended healthcare cost range 214 may together represent the healthcare costs of Y % of patients in the age group D, where Y is greater than X.

Figure 3:
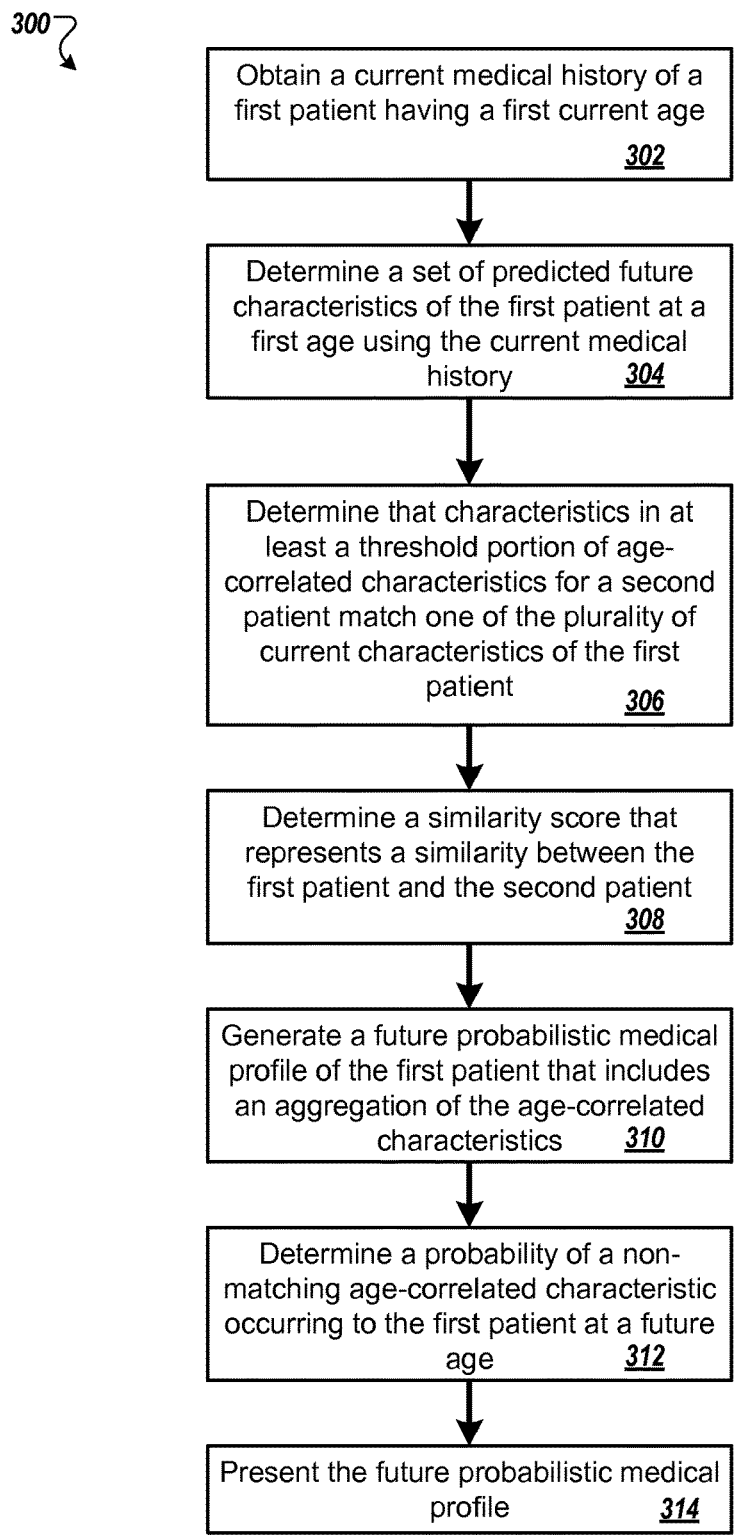
FIG. 3 is a flow diagram of an example process of generating a future medical profile of a first patient.

FIG. 3 is a flow diagram of an example process 300 for generating a future medical profile of a first patient. The process can be implemented by a medical profile system that includes one or more appropriately programmed computer programs installed on one or more computers.

The medical profile system obtains (302) a current medical history of a first patient having a first current age. The current medical history includes multiple current characteristics of the first patient, e.g., one or more of a demographic, e.g., a biological statistic, for the first patient, medical diagnosis of the first patient, a record of a medical procedure performed on the first patient, a characterization of a hospital visit of the first patient, a record of a medication for the first patient, a family history of the first patient, or any combination of two or more of these. For example, the medical profile system determines that a thirty-five year old male has hypertension and high cholesterol.

The medical profile system optionally determines (304) a set of predicted future characteristics of the first patient at a first future age using the current medical history. The future characteristics may include a possible medical diagnosis of the first patient, a potential medical procedure that may be performed on the first patient, a characterization of a future hospital visit of the first patient, and a potential future medication for the first patient. Additional details and examples of the future characteristics of the first patient are described below in reference to FIG. 4A.

The medical profile system determines (306) that characteristics in at least a threshold portion of age-correlated characteristics for a second patient match one of the current characteristics of the first patient.

In some implementations, the medical profile system includes a database of medical profiles for multiple different patients and determines that some of the predicted future characteristics of the first patient at the future age, e.g., the potential future characteristics 402, are the same as age-correlated characteristics of other patients, including the second patient, at a second age. For instance, the second age may be the same age as the future age, e.g., forty years old, and/or may be the current age of some of the other patients.

The medical profile system identifies each of the patients in the group of other patients separately. For example, the medical profile system compares the characteristics of the second patient with the characteristics of the first patient independently from a comparison of characteristics of a third patient with the characteristics of the first patient.

The medical profile system determines whether a predetermined threshold number of characteristics for a second patient match, e.g., is the same as, characteristics of the first patient. The predetermined threshold may be a percentage of characteristics, e.g., at least fifty or seventy-five percent of the characteristics must be the same. The predetermined threshold may be a quantity of characteristics, e.g., at least five or ten characteristics of the second patient must be the same as characteristics of the first patient.

In some implementations, the medical profile system may map characteristics to a multi-dimensional space when determining whether the threshold portion of age-correlated characteristics for the second patient match a portion of the set of future characteristics and identifying other patients. Details and examples of mapping the characteristics to the multi-dimensional space will be described below in reference to FIG. 4B.

The medical profile system may predict a respective future medical profile for each of the other patients. Details and examples of the other future medical profiles will be described below in reference to FIGS. 4C-D.

The medical profile system determines (308) a similarity score that represents a degree of similarity between the first patient and the second patient. For example, the medical profile system may use the age-correlated characteristics of the second patient to determine the similarity score. The medical profile system may determine a similarity score for each of the other patients.

In some implementations, the medical profile system determines a ratio of a first quantity of matching age-correlated characteristics from the respective set of age-correlated characteristics to a second quantity of non-matching age-correlated characteristics from the respective set of age-correlated characteristics for the second patient. The medical profile system then uses the ratio to determine the similarity score for the second patient. For instance, when the first quantity of matching age-correlated characteristics of a particular other patient is five and the second quantity of non-matching age-correlated characteristics is ten, the similarity score for the particular other patient is $5/10=0.5$.

The medical profile system may determine a similarity score using a percentage of the matching age-correlated characteristics out of the total age-correlated characteristics of a particular other patient. For example, when the quantity of matching age-correlated characteristics of a particular other patient is five and the total quantity of age-correlated characteristics is fifteen, the similarity score for the particular other patient is $5/15=0.33$.

The medical profile system generates (310) a future probabilistic medical profile of the first patient that includes an aggregation of at least a portion of the age-correlated characteristics. Details and examples of the future probabilistic medical profile will be described below in reference to FIG. 4D. The aggregation may include at least one non-matching age-correlated characteristic that does not match any of the current characteristics of the first patient.

The medical profile system may determine (312) a probability of a non-matching characteristic of a particular other patient, e.g., congestive heart failure or having a pacemaker, occurring to the first patient at another future age. For instance, if two of ten other patients, with age-correlated characteristics that match the set of future characteristics of the first patient, have or are predicted to have congestive heart failure, the medical profile system may determine that the first patient has a twenty percent chance of having congestive heart failure.

The probability of the non-matching characteristic may be determined using the similarity scores for the respective other patients. For example, if one of the ten other patients has a pacemaker and that particular other patient has a similarity score of sixty-three percent, the probability of the first patient requiring a pacemaker may be estimated as $10\%\times63\%=6.3\%$. The medical profile system may aggregate the respective similarity scores to determine an overall probability of the non-matching characteristic, e.g., by adding the similarity scores and dividing by the total quantity of other patients.

The medical profile system presents (314) the future probabilistic medical profile. The presentation may include a range of characteristics of the future probabilistic medical profile, e.g., selected from age $t_1$ to ten years after, $t_1+10$, or may be for a specific age of the first patient, e.g., $t_1+7$.

In some implementations, the process 300 can include additional steps or fewer steps. Some of the steps can be divided into multiple steps. For example, the medical profile system may perform steps 302-306 and 310 without performing steps 308, 312, and/or 314.

Figure 4A:
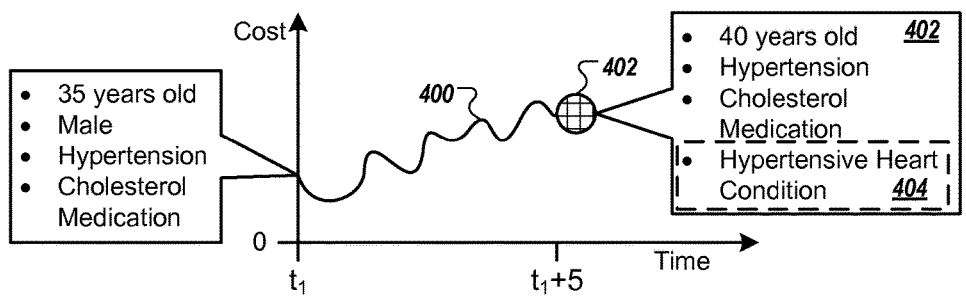
FIG. 4A shows an example of an initial projected medical profile of the first patient.

FIG. 4A shows an example of a cost projection 400 of the first patient. The initial cost projection 400 includes an age-based cost estimate of the first patient, e.g., for a given age, what illnesses may afflict the first patient, and a likelihood that the first patient is going to suffer from each of the illnesses, and a cost associated with the illnesses as a function of age. In the example shown, the initial cost projection 400 includes costs associated with potential future characteristics 402 of hypertension, high cholesterol, and hypertensive heart condition when the patient is at age forty.

The initial cost projection 400 may be for a predetermined time period from the patient's current age, at $t_1$, to a future age of the patient, at $t_1+5$. In this example, the current age of the patient is thirty-five and the future age is forty. In some implementations, the future age may be between three to eight years more than the current age or more, e.g., an estimated age at which the patient will die.

In some implementations, the medical profile system may determine a likelihood that the first patient will have each of the future characteristics. In this example, the likelihood of the first patient having hypertension and high cholesterol are high, e.g., since the first patient currently has these characteristics, and the likelihood that the first patient will have hypertensive heart condition is lower, e.g., since hypertensive heart condition is a predicted characteristic 404 that the patient currently does not have.

Figure 4B:
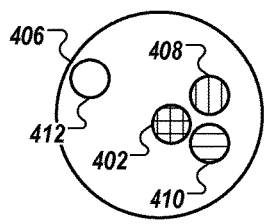
FIG. 4B shows an example mapping of patient's characteristics to a multi-dimensional space.

FIG. 4B shows an example mapping 406 of patient's characteristics to a multi-dimensional space. The mapping 406 includes the potential future characteristics 402 of the first patient, a second set of characteristics 408 of a second patient, and a third set of characteristics 410 of a third patient, when the determined group of other patients includes both the second patient and the third patient.

The medical profile system may use a predetermined threshold distance to determine whether the threshold portion of age-correlated characteristics for the other patients match the portion of the set of future characteristics. The medical profile system may determine that a distance between the second set of characteristics 408 and the third set of characteristics 410 is within the predetermined threshold distance. In addition, the system can determine that a distance between the second set of characteristics 408 and a fourth set of characteristics 412 is not within the predetermined threshold distance and should not be used to generate a future medical profile for the first patient. The medical profile system may use a pre-specified threshold distance d to identify the group of other patients and the corresponding characteristics. Example techniques of determining a distance between sets of characteristics will be described below in reference to Calculation (1).

The medical profile system may use a predetermined quantity q of nearest neighbors in the mapping 406 to generate the future medical profile for the first patient. For example, the medical profile system may identify five-hundred or one thousand sets of patient characteristics in the mapping 406 that have the shortest distance from the potential future characteristics 402 of the first patient. The medical profile system may use a quantity q of nearest neighbors to generate the future medical profile for the first patient.

The medical profile system may determine a respective medical history for each of the other patients and use the respective medical histories when identifying the patients in the group of other patients and the age-correlated characteristics of the other patients. For example, the medical profile system may determine that a second threshold portion of age-correlated characteristics from each of the other medical histories match a second portion of the characteristics from the initial cost projection 400 for an age range of the first patient and the other patients from the current age of the first patient to the future age of the first patient. In this example, the medical profile system determines whether a patient's initial cost projection 400 is similar to, or partially the same as, another patient's medical history.

The threshold portion of age-correlated characteristics that match the second portion of characteristics from the initial cost projection 400 may be for a specific age or age range. For example, the medical profile system may determine that a threshold portion of age-correlated characteristics match a portion of characteristics for each year in the initial cost projection 400. In some implementations, the medical profile system may determine that a threshold portion of age-correlated characteristics match a portion of characteristics for all of the characteristics and across all years of the initial projected medical profile 400.

In some implementations, the medical profile system may determine that a threshold portion of age-correlated characteristics for each of the other medical histories match a portion of characteristics from the current medical history of the first patient for a predetermined age or age range of the other patients and the first patient. For example, the medical profile system may determine that the medical histories of the first patient and another particular patient are similar or the partially the same for the predetermined age range, e.g., that some of the characteristics in both medical histories match. The predetermined age range may be from an age three to five years younger than the current age of the first patient and for the same age range in the other particular patient. In some examples, when the first patient is thirty-five, the predetermined age range may be from the age of thirty to thirty-five for both the first patient and the other particular patient.

In some implementations, the medical profile system determines that a threshold portion of age-correlated characteristics from another medical history of another patient at a specific age, e.g., the current age of the first patient, are the same as a portion of current characteristics from the current medical history for the first patient, e.g., at the same age. For example, the medical profile system may determine that the first patient, who is thirty-five, currently has hypertension and high cholesterol and that when the second patient was thirty-five the second patient had hypertension and high cholesterol.

Figure 4C:
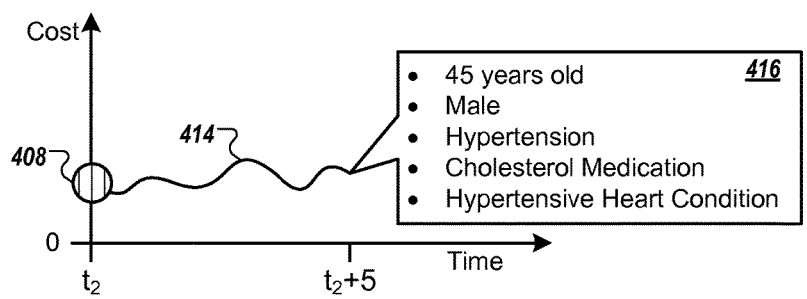
FIGS. 4C-E show example future medical profiles of patients.

FIG. 4C shows an example of a second cost projection 414 for the second patient from a $t_2$ to $t_2+5$. The cost projection 414 includes age-based characteristics of the second patient, e.g., at a given age, what illnesses may afflict the second patient, a likelihood that the second patient is going to suffer from each of the illnesses, a projected cost associated with the illnesses, or any combination of the above. The second patient may be the same age at $t_2$ as the first patient at time $t_1+5$, e.g., forty years old. The age of the second patient at $t_2$ may be the second patient's current age, a previous age, or a future age, e.g., in one to three years or less.

The second cost projection 414 includes potential future characteristics 416 of the second patient at a specific time $t_2+5$. In this example, the potential future characteristics 416 of the second patient are the same as the potential future characteristics 402 of the first patient.

Figure 4D:
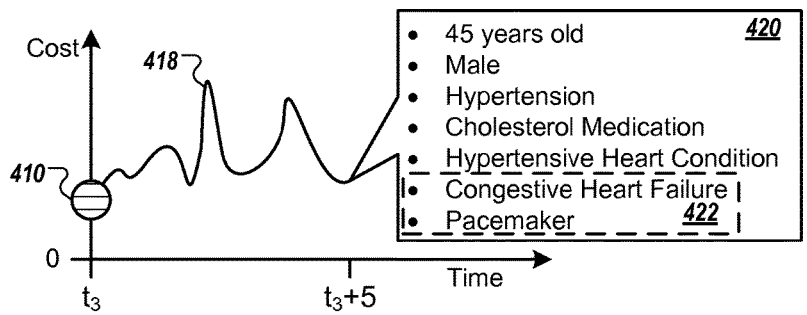

The medical profile system may determine a third future cost projection 418 for the third patient from $t_3$ to $t_3+5$, shown in FIG. 4D, in the database of medical profiles or another database. The third cost projection 418 includes age-based cost associated with potential future characteristics 420 of the third patient at a particular time $t_3+5$ and one or more predicted characteristics 422 of the third patient, e.g., that are not included in the potential future characteristics 402 of the first patient.

The medical profile system may generate the second future medical profile 414 and the third future cost projection 418 using the other medical histories of the corresponding other patients, e.g., the second medical history and the third medical history respectively. The future medical profiles may be generated using the process 300 or another appropriate algorithm.

Figure 4E:
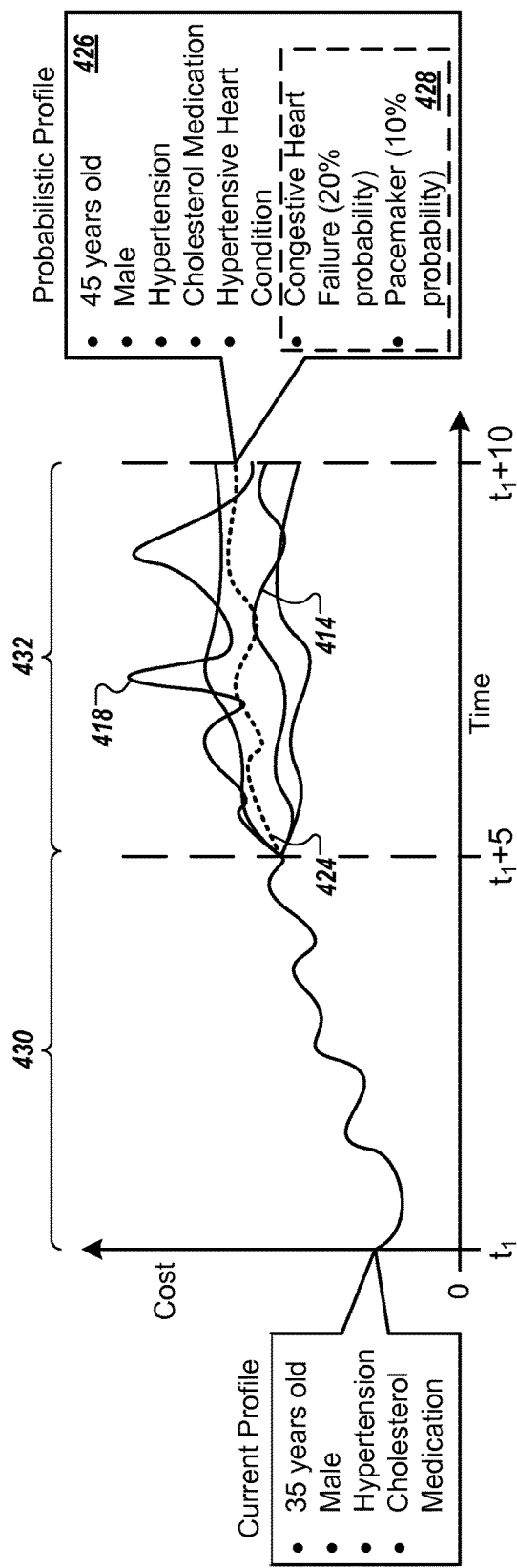

FIG. 4E shows an example future cost projection 424 for the first patient. The future cost projection 424 is represented as a curve that is a function of age. Each point of the curve can include a set of characteristics of the first patient at a specific age, an estimated medical expense associated with the set of characteristics, or both. The medical profile system may present the future medical profile 424 in a user interface on a display device. For example, the medical profile system may weight each of the age-correlated characteristics of the other patients using the corresponding similarity score and aggregate all of the age-correlated characteristics for each of the other patients to generate the future cost projection 424 for the first patient from the first patient's current age at $t_1$ to another future age later than the first future age, e.g., $t_1+10$. The other future age may be between eight and fifty years more than the first patient's current age. In some implementations, the future cost projection 424 may include characteristics for a portion of or all of the first patient's life expectancy.

The future medical profile may be an aggregation of a portion of the other medical histories and the other future medical profiles of the other patients. For example, a first portion 430 of the future cost projection 424 may be based on the other medical histories, a second portion 432 of the future cost projection 424 may be based on the other medical histories and the other future medical profiles, e.g., based on different current ages for the other patients, and a third portion 430 of the future cost projection 424 may be based on the other future medical profiles. In some implementations, the first portion 430 of the future cost projection 424 may be determined using the initial projected medical profile 400 of the first patient.

The future cost projection 424 may include a deterministic profile, a probabilistic profile 426, or both, of the first patient at a particular age. For example, the future cost projection 424 may include a separate probabilistic profile for each age of the first patient from $t_1$ to $t_1+10$, including the probabilistic profile 426 at $t_1+10$. The probabilistic profile 426 includes a set of characteristics that the first patient is projected to have at age $t_1+10$. Each of the characteristics, e.g., medical condition, may occur at a probability that is higher than a threshold. The medical profile system may present the probabilistic profile 426 of the first patient for display in a textual or graphical user interface on a display device.

In some implementations, the future cost projection 424 may be generated from an average of the age-correlated characteristics of the other patients, e.g., using a total quantity of the other patients.

The future cost projection 424 includes a second probabilistic profile 428 of the first patient. For example, if one of the ten other patients has a pacemaker, the medical profile system may determine that the first patient has a ten percent chance of having a pacemaker, e.g., as indicated by the second probabilistic profile 428. The medical profile system may present the first probabilistic profile 426 and second probabilistic profile 428 of the first patient for display in a textual or graphical user interface on a display device.

The user interface may include an indication of the non-matching age-correlated characteristic and the corresponding probability of the non-matching age-correlated characteristics occurring to the first patient at the other future age, e.g., one or more of the second probabilistic profile 428 of the first patient at $t_1+10$ or a different age.

The medical profile system may determine an estimated future healthcare cost for the first patient using the future cost projection 424. The medical profile system may determine the estimated future healthcare cost using other medical histories. The medical profile system may periodically update the estimated future healthcare cost using changes to the costs of healthcare services or products. The estimated future healthcare cost may include separate annual costs for each year from the first patient's current age to the second future age and/or an overall cost from $t_1$ to $t_1+10$.

Figure 5:
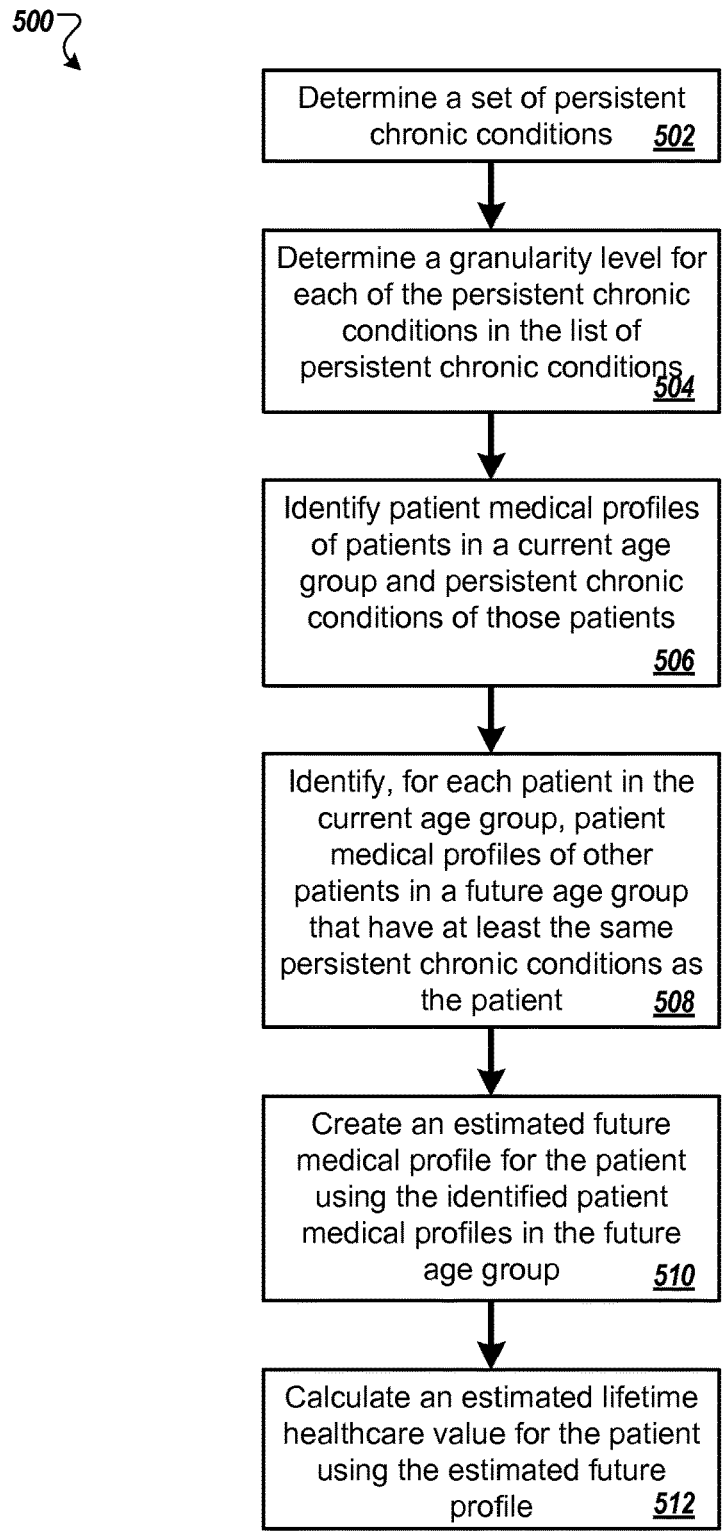
FIG. 5 is a flow diagram of an example process of estimating a lifetime healthcare value.

FIG. 5 is a flow diagram of an example process 500 for estimating a healthcare value for a patient. The process 500 can be implemented by a medical profile system that includes one or more appropriately programmed computer programs installed on one or more computers. The medical profile system may perform the process 500 in conjunction with or instead of the process 300 or may perform some steps from each of the processes.

The medical profile system determines (502) a set of persistent chronic conditions. A condition may be classified by the system to be a persistent chronic condition if at least seventy percent of patients who are diagnosed with the condition receive another diagnosis of the same condition at a future time, e.g., during another consultation that is not part of an initial consultation within a year of the first diagnosis of the condition. For example, if at least seventy percent of patients experience acute asthma exacerbation multiple times in two consecutive years, the medical profile system may classify acute asthma exacerbation as a persistent chronic condition.

The medical profile system determines (504) a granularity level for each of the persistent chronic conditions. For instance, the medical profile system may separate related persistent chronic conditions when a patient diagnosed with a first persistent chronic condition has substantially different healthcare values, e.g., costs, than another patient diagnosed with a second, related persistent chronic condition. The medical profile system may group related persistent chronic conditions in a single condition category when the healthcare values are not substantially different.

In some implementations, the medical profile system may use a hierarchy of codes for the persistent chronic conditions, e.g., International Classification of Diseases, Ninth Revision, Clinical Modification (ICD-9-CM) codes, which indicate categories of conditions and specific etiologies, anatomic sites, or manifestations of the conditions. For instance, the first three digits of an ICD-9-CM code may indicate a condition category and the digits after the decimal point may indicate the etiology, anatomic site, or manifestation of the condition.

The distinction between aneurysm of heart wall, e.g., with an ICD-9-CM code of 414.10, and aneurysm of coronary vessels, e.g., with an ICD-9-CM code of 414.11, may be small in terms of the healthcare values associated with these conditions, and the system may therefore include the two conditions may in the same condition category. The medical profile system may execute a z-test to compare two distributions of future healthcare values of patients, one with aneurysm of heart wall and one with aneurysm of coronary vessels. If the results of the z-test are statistically significant, the medical profile system may keep the separate conditions in separate categories for patients' medical profiles. If the results of the z-test are not statistically significant, the medical profile system may aggregate the two conditions into a single condition category.

The medical profile system identifies (506) patient medical profiles of patients in a current age group and persistent chronic conditions of those patients. The persistent chronic conditions may include condition categories, e.g., determined in step 504, for some of the persistent chronic conditions.

The medical profile system determines the persistent chronic conditions for the patients in the current age group. The current age group may be one of the age groups 202 A-G shown in FIG. 2 above. Some examples of persistent chronic conditions are diabetes, hypertension, high cholesterol, hypertensive heart condition, congestive heart failure, asthma, and rheumatoid arthritis. Additional details and examples of the patient medial profiles are described below in reference to FIG. 6.

The medical profile system identifies (508), for each particular patient in the current age group, patient medical profiles of other patients in an older age group that have the same persistent chronic conditions as the particular patient. The medical profile system uses the particular patient's current medical profile to identify multiple other patients that belong to the future age group, e.g., the next age group, and that have persistent conditions that are the same as or similar to the conditions in the particular patient's medical profile. For instance, if the current age group is the age group B, shown in FIG. 2, the future age group may be the age group C or the age group D. The other patients may or may not have the same sex as the patient.

The medical profile system may determine a similarity score using a special asymmetric distance metric. For example, vectors x and y represent n possible persistent chronic conditions of two separate patients j, and k. Vectors x and y may have binary values indicating whether or not the patient has the corresponding persistent chronic condition determined in step 504 above. In some implementations, vectors x and y may be real valued vectors indicating a likelihood the patient has the corresponding persistent chronic condition. The similarity score dist(x, y) can be defined using Calculation (1) below.

$$dist(x, y) = \begin{cases} \infty, & \forall\, i\,|\,x_i = 1 \text{ and } y_i = 0 \\ \max_{\forall i: x_i > 0}(\text{abs}(x_i - y_i)), & \text{otherwise} \end{cases} \quad (1)$$

In Calculation (1), $i \in \{1, \ldots, n\}$, $x_i=1$ indicates that patient j has persistent chronic condition i, $x_i=0$ indicates that patient j does not have and is not predicted to have persistent chronic condition i, $x_i=a$, where $0<a<1$, indicates an estimated probability that patient j may be diagnosed with persistent chronic condition i in the future, and abs $(x_i-y_i)$ indicates an estimated probability that patient j will have persistent chronic condition i in the future, wherein abs $(x_i-y_i)=0$ indicates that the patient j currently has persistent chronic condition i and abs $(x_i-y_i)=b$ indicates a b % estimated probability that patient j will have persistent chronic condition i in the future.

In Calculation (1), the medical profile system assigns a distance of ∞ between the vector y and the vector x when the patient k does not have any one of the persistent chronic conditions with which patient j is diagnosed. However, the patient k may be allowed to have some other persistent chronic diagnoses with which the patient j is not diagnosed as long as patient k also has the same persistent chronic diagnoses of patient j.

The medical profile system compares each of the patient profiles in the future age group separately with that of the particular patient. For example, the medical profile system compares the conditions of the particular patient with the conditions of a patient in the older age group independently from a comparison of conditions of another patient in the older age group with the conditions of the particular patient.

The medical profile system creates (510) an estimated future medical profile for the patient using the identified patient profiles in the future age group. For example, the medical profile system may use the persistent chronic conditions of the other patients, including estimated future medical profiles for the other patients, to generate an estimated future medical profile for the particular patient for the future age group, e.g., an estimated future medical profile for the particular patient when the particular patient will belong to the future age group, such as the next age group. For example, the medical profile system may weight each of the other patients' medical conditions, e.g., using a degree of similarity determined with Calculation (1), and aggregate the weighted medical conditions together to determine the estimated future medical profile for the particular patient.

In some implementations, for a patient j in age group t, with a current medical profile $x^{j,t}$, the medical profile system may determine an estimated future medical condition $x_i^{j,t+1}$ for a future age group t+1 and a persistent chronic condition i using Calculation (2) below.

$$x_i^{j,t+1} = \frac{\sum_{y \in N_{j,t}} y_i(1 - dist(x^{j,t}, y))}{\sum_{y \in N_{j,t}} (1 - dist(x^{j,t}, y))} \quad (2)$$

In Calculation (2), the patient group $N_{j,t}$ includes all vectors y for patients k where agegroup(y)=t+1, and dist($x^{j,t}$,y)<∞. In various implementations, age group t+1 may be an age group that is one year older than age group t, or an age group in a next bin. In the latter case, for example, if age group t is an age group of 36-40 years old, age group t+1 may be 41-45 years old. The vectors y in the patient group $N_{j,t}$ may be defined by gender(y)=gender($x^j$) where each patient k has the same sex as the patient j. The medical profile system may combine some or all of the separate estimated future medical conditions $x_i^{j,t+1}$ for the patient j to determine an estimated future medical profile $x^{j,t+1}$ for the patient j, e.g., where the estimated future medical profile is a vector with one value for each persistent chronic condition i.

For example, the medical profile system may evaluate all patients that have the same sex, are in the next age group, and have all the persistent chronic conditions with which the particular patient is diagnosed. They may have some additional diagnoses. For each persistent chronic condition, from those identified in step 502 above, the medical profile system calculates a similarity-weighted average to determine a probability that the particular patient will have the respective persistent chronic condition. The use of Calculations (1) and (2) may ensure that the medical profile system maintains all the previously diagnosed persistent chronic conditions of the particular patient while predicting a probability that the particular patient will have other persistent chronic conditions.

Optionally, instead of using all other patients that satisfy Calculation (1) above to generate the estimated future medical profile, the medical profile system may use a predetermined quantity q of nearest neighbors to generate the future medical profile for the particular patient. For example, the medical profile system may identify five-hundred or one-thousand medical profiles in step 508 that have the shortest distance from the particular patient's current medical profile or the greatest similarity scores with the particular patient's current medical profile. The medical profile system may use any appropriate quantity q of nearest neighbors to generate the future medical profile for the first patient. The medical profile system calculates (512) an estimated lifetime healthcare value for the patient using the estimated future profile, for example, by aggregating, over years, a projected value associated with medical condition of the patient in each year. The estimated lifetime healthcare value may be, for example, an estimated lifetime healthcare cost. The medical profile system may calculate corresponding estimate lifetime healthcare values for each patient in the current age group.

The medical profile system may present the estimated future medical profile of a particular patient to a user, analyze the estimated future medical profile of the particular patient to determine an estimated lifetime healthcare value or an annual estimated healthcare value for the particular patient, e.g., and a value category to which the particular patient will belong, or determine potential preventative measures that the particular patient may take to reduce the likelihood of predicted future medical conditions. The medical profile system may present the estimated lifetime healthcare value, the annual estimated healthcare value, and/or the potential preventative measures to the user instead of or in addition to the estimated future medical profile.

In some implementations, the process 500 includes additional steps or fewer steps. Some of the steps can be divided into multiple steps. For example, the medical profile system may perform steps 506-510 for patients in multiple different age groups. The medical profile system may perform steps 506-510 without performing steps 502-504 and 512. The medical profile system may perform the process 500 for a single patient, e.g., by identifying patient medical profiles of other patients in the future age group for only the single patient.

In some implementations, the medical profile system may perform the process iteratively for one or more patients. For example, the medical profile system may perform steps 506-510 for a single patient across multiple different future age groups to generate a composite medical profile for the patient into the future, e.g., until a final age group, such as the age group F shown in FIG. 2, is reached. For each iteration after the initial iteration, the medical profile system may incorporate the probabilities of determined persistent chronic conditions for the patient into the patient's medical profile and use these predicted persistent chronic conditions when estimating additional persistent chronic conditions for the patient.

For instance, when the medical profile system determines that the patient, e.g., in age group B, has an estimated thirty-three percent change of hypertensive heart condition in a next age group, e.g., age group C, the medial profile system may determine other future medical profiles for patients in a second future age group, e.g., age group D, that have all of the same persistent chronic conditions with which the patient is currently diagnosed, e.g., hypertension and high cholesterol, but might not have hypertensive heart condition. The future medical profile system uses these other determined future medical profiles to determine a second estimated future medical profile for the patient, e.g., in addition to using the first estimated future medical profile to determine the second estimated future medical profile.

FIG. 6 shows an example table 600 of patient medical profiles. The table 600 includes medical profiles 602a-b for patient 2, and medical profiles 604, 606, 608, and 610 for patients 4, 6, 8, and 10, respectively. The table 600 indicates, for multiple persistent chronic conditions, whether the corresponding patient current has the condition, e.g., with a value of one, does not have the condition, e.g., with a value of zero, or is predicted to have the condition at a future time, e.g., with a value between zero and one.

The similarity score between the particular patient 2 and patients 4, 6, and 8, is zero, indicating a high similarity, as determined using Calculation (1). For instance, the medical profile system may determine dist(2,4)=0 for patients 2 and 4 although patient 4 has an additional diagnosis, e.g., hypertensive heart condition, with which the particular patient 2 was not diagnosed, because patient 4 has all of the conditions with which patient 2 was diagnosed. The medical profile system determines, using Calculation (1), that the particular patient 2 and patient 10 are not similar, e.g., dist(2,10)=∞, since patient 10 does not have hypertension. Based on the similarity scores, the medical profile system will use the medical profiles 602a, 604, 606, and 608 when determining an estimated future medical profile 602b for the particular patient 2, e.g., for time $t_{0+5}$ which indicates a particular age group to which the patient 2 will belong.

In some implementations, the medical profile system may use any values to represent a similarity between two patients. For example, lower numerical values may represent a higher similarity.

The medical profile system uses the estimated future medical profile 602b to determine that the particular patient 2's average annual healthcare cost is estimated to increase from $18,000 to $24,000 when moving from the particular patient 2's current age group, which includes the age thirty-five, to the future age group, which includes the age forty.

In some implementations, the similarity scores are directional. For example, dist(2,4)=0 but dist(4,2)=∞ because patient 2 does not have hypertensive heart condition while patient 4 is diagnosed with hypertensive heart condition.

Figure 7:
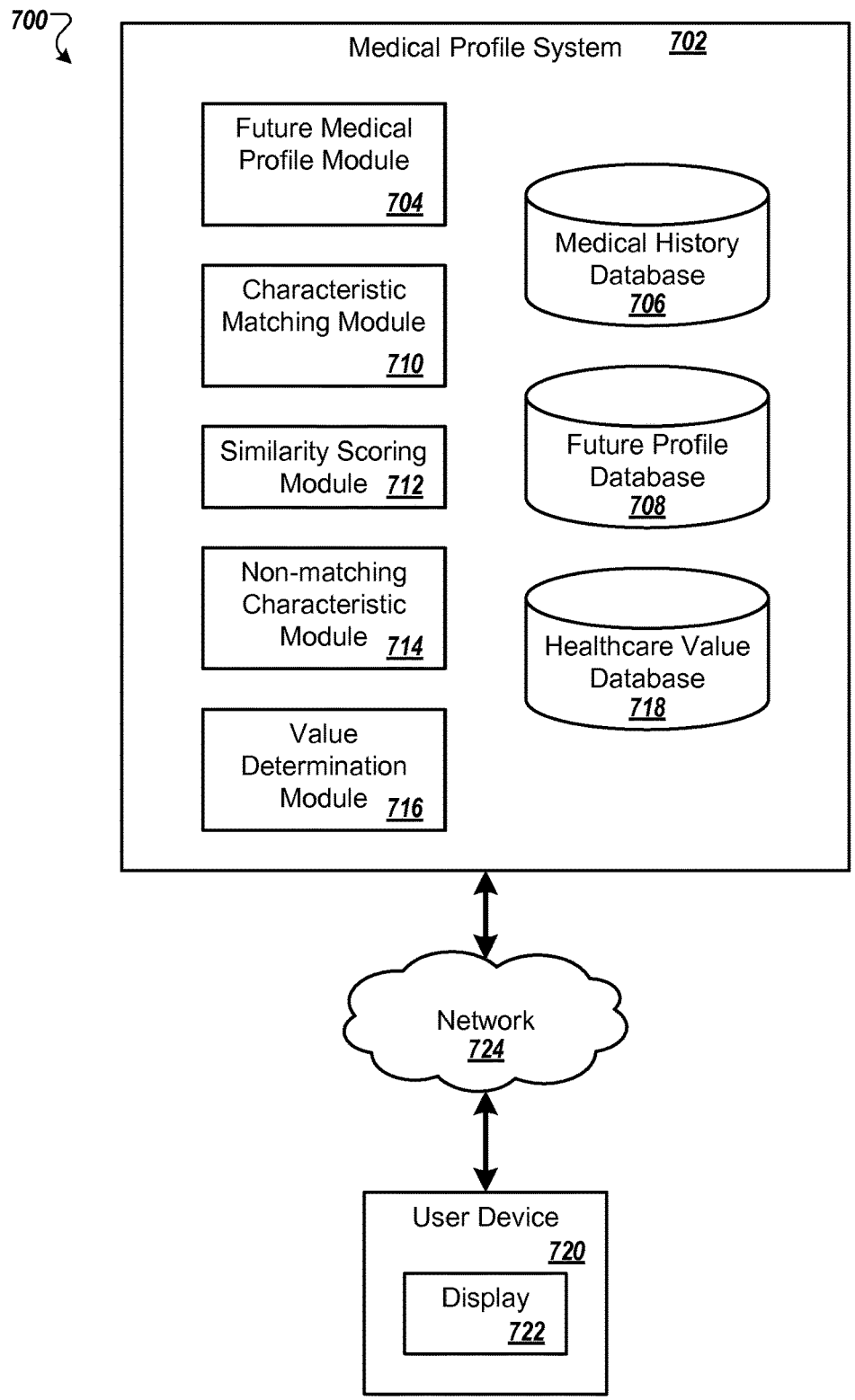
FIG. 7 illustrates an example system for generating a future medical profile of a patient.

FIG. 7 illustrates an example system 700 for generating a future medical profile of a patient. A medical profile system 702 includes a future medical profile module 704 that accesses a medical history database 706 to generate an initial future medical profile for the patient and stores the initial future medical profile in a future profile database 708.

A characteristic matching module 710 of the medical profile system 702 compares characteristics, e.g., persistent chronic conditions, from the initial future medical profile to characteristics from other patients' medical histories, in the medical history database 706, and other patient's future medical profiles, in the future profile database 708. The characteristic matching module may determine whether or not a threshold portion of characteristics for another patient match a portion of the characteristics from the patient's initial future medical profile. In some implementations, the characteristic matching module 710 may determine a list of persistent chronic conditions and/or group the persistent chronic conditions based on a level of granularity.

Once the characteristic matching module 710 determines that a threshold portion of characteristics for another patient match the portion of characteristics from the patient's future medical profile, a similarity scoring module 712 of the medical profile system 702 determines a similarity score for one or more other patients and the patient, e.g., using Calculation (1).

The future medical profile module 704 of the medical profile system 702 may generate a future medical profile for the patient using the characteristics of the matching other patients, e.g., using Calculation (2). The future medical profile module 704 stores the future medical profile in the future profile database 708. The future medical profile module 704 may replace the initial future medical profile with the future medical profile or may store both the initial and one or more future medical profiles in the future profile database 708, e.g., to track a sequence of updated future medical profiles for the patient.

A non-matching characteristic module 714, or the future medical profile module 704, may determine, for another patient that has a threshold portion of characteristics that match characteristics from the first patient's initial future medical profile, a non-matching characteristic. The non-matching characteristic module 714 may store an identification of the non-matching characteristic, and a corresponding probability of the non-matching characteristic occurring in the patient, in the future profile database 708.

A value determination module 716 may access the medical history database 706 and/or a healthcare value database 718 in addition to the future profile database 708 to determine a predicted healthcare value for the patient. The predicted healthcare value can include a predicted healthcare cost.

The medical profile system 702 may send the future medical profile and/or the predicted healthcare value to a user device 720, e.g., a personal computer, electronic tablet, mobile telephone, or the like. The user device 720 may present the received data on a display 722, e.g., a monitor or a touch screen display.

The user device 720 may be configured to send data to and receive data from the system 702 over a network 724. The network 724 may be a local area network (LAN), a wide area network (WAN), the Internet, or a combination of them. In some implementations, the medical profile system 702 is directly connected to the user device 720.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method comprising:
receiving, from a user, a request to compute a predicted future medical profile for a first patient having a future age N that is at least M*2 years beyond an initial age a1 using only M years of data, wherein the future medical profile assigns a score to each of a plurality of characteristics, each score for each characteristic representing a respective likelihood of the first patient having the respective characteristic at the future age N;
obtaining, by one or more computers, a current medical history of the first patient, the current medical history comprising data representing a plurality of current characteristics of a first patient having an initial age a1, a1 being less than N;
determining, using the current medical history of the first patient, an initial predicted medical profile of the first patient at a future time when the first patient will have a second age a2, wherein the second age a2 is no more than M years beyond the initial age a1;
obtaining M years of medical history for a plurality of other patients starting at a respective time when each of the other patients has a respective age that is at least the second age a2 and covering a respective time at which each of the other patients has attained the age N, wherein each medical history for each of the other patients indicates a respective age at which a particular characteristic occurred for the other patient;
computing a plurality of nearest neighbors to the first patient, each nearest neighbor having respective characteristics occurring at the second age a2 that are most similar to the initial predicted medical profile of the first patient at the future time at which the first patient has the second age a2;
adding, to the predicted future medical profile for the first patient, one or more non-matching characteristics that each occur in at least one respective medical history of a respective nearest neighbor of the plurality of nearest neighbors but that does not occur in the medical history of the first patient;
generating a respective score for each of the one or more non-matching characteristics that each occur in at least one respective medical history of a respective nearest neighbor of the plurality of nearest neighbors but that does not occur in the medical history of the first patient, wherein the score for each non-matching characteristic represents a measure of how frequently the non-matching characteristic occurs in the medical histories of the plurality of nearest neighbors;
generating a presentation of the future medical profile for the first patient, the presentation including data representing a range of predicted outcomes for each of the one or more non-matching characteristics and a respective score for each of the one or more non-matching characteristics; and
providing the presentation of the future medical profile for the first patient for display on a display device to the user.

2. The method of claim 1, wherein:
generating the respective score for each of a plurality of non-matching characteristics comprises determining, by the one or more computers for each of the non-matching characteristics, a probability of the non-matching characteristic occurring to the first patient at the age N.

3. The method of claim 2, comprising:
determining one or more potential preventative measures for one of the non-matching characteristics that does not occur in the current medical history of the first patient; and
presenting, by the one or more computers, data for one or more potential preventative measures, an indication of the one of the non-matching characteristics, and the corresponding probability of the one of the non-matching characteristics occurring to the first patient.

4. The method of claim 2, wherein determining the probability of the non-matching characteristics occurring to the first patient at the age N comprises:
determining, for each nearest neighbor having at least one of the non-matching characteristics, a respective similarity score that represents a degree of similarity between the corresponding nearest neighbor and the first patient; and
aggregating, for each of the non-matching characteristics, the similarity scores to determine the probability of the non-matching characteristic occurring to the first patient at the age N.

5. The method of claim 4, wherein determining, for each nearest neighbor having at least one of the non-matching characteristics, the respective similarity score that represents the degree of similarity between the corresponding nearest neighbor and the first patient comprises:

determining a ratio of i) a first quantity of matching characteristics that occur in both the respective predicted medical profile of the corresponding nearest neighbor and the current medical history of the first patient to ii) a second quantity of non-matching characteristics that occur in the respective predicted medical profile of the corresponding nearest neighbor but that do not occur in the current medical history of the first patient; and determining the respective similarity score using the corresponding ratio.

6. The method of claim 1, comprising:

determining, by the one or more computers and for each of the nearest neighbors, a respective second medical history; and determining an estimated future healthcare value for the first patient using the predicted medical profiles and the second medical histories for the nearest neighbors.

7. The method of claim 6, wherein:

determining the estimated future healthcare value for the first patient using the predicted medical profiles and the second medical histories for the nearest neighbors comprises determining, for each year from the first age of the first patient to the age N of the first patient, an estimated healthcare value.

8. The method of claim 6, wherein:

computing the plurality of nearest neighbors comprises computing the plurality of nearest neighbors for which at least a threshold quantity of characteristics occur in both the second medical history for the corresponding nearest neighbor and in the current medical history of the first patient for a predetermined age range of the nearest neighbors and the first patient.

9. The method of claim 8, wherein the predetermined age range is from a younger age to the first age, and the younger age comprises an age three to five years younger than the first age.

10. The method of claim 6, comprising:

determining a current set of characteristics for the first patient at the first age from the current medical history;

determining, for each second medical history of one of the nearest neighbors, a set of characteristics for the respective nearest neighbor at the first age; and determining that each characteristic in at least a threshold portion of characteristics from each of the sets of characteristics matches a corresponding characteristics in the current set of characteristics for the first patient.

11. The method of claim 6, further comprising generating a ranking of the non-matching characteristics using a weighted average of probabilities of the characteristics occurring to the first patient.

12. The method of claim 6, wherein further comprising generating a ranking of the non-matching characteristics using an aggregation of a) at least a portion of each of a plurality of second medical histories, each second medical history for a respective nearest neighbor, and b) at least a portion of the predicted medical profiles for one or more of the nearest neighbors.

13. The method of claim 1, wherein the current characteristics of the current medical history comprise one or more of biological statistics for the first patient, a medical diagnosis of the first patient, a record of a medical procedure performed on the first patient, a characterization of a hospital visit of the first patient, a record of a medication for the first patient, or a family history of the first patient.

14. The method of claim 1, comprising:

generating a second predicted medical profile of the first patient that includes an aggregation of at least a portion of the predicted medical profiles for the nearest neighbors.

15. A non-transitory computer storage medium storing instructions that, when executed by one or more computers, cause the one or more computers to perform operations comprising:

receiving, from a user, a request to compute a predicted future medical profile for a first patient having a future age N that is at least M*2 years beyond an initial age a1 using only M years of data, wherein the future medical profile assigns a score to each of a plurality of characteristics, each score for each characteristic representing a respective likelihood of the first patient having the respective characteristic at the future age N;

obtaining, by at least one of the computers, a current medical history of the first patient, the current medical history comprising data representing a plurality of current characteristics of a first patient having an initial age a1, a1 being less than N;

determining, using the current medical history of the first patient, an initial predicted medical profile of the first patient at a future time when the first patient will have a second age a2, wherein the second age a2 is no more than M years beyond the initial age a1;

obtaining M years of medical history for a plurality of other patients starting at a respective time when each of the other patients has a respective age that is at least the second age a2 and covering a respective time at which each of the other patients has attained the age N, wherein each medical history of each of the other patients indicates a respective age at which a particular characteristic occurred for the other patient;

computing a plurality of nearest neighbors to the first patient, each nearest neighbor having respective characteristics occurring at the second age a2 that are most similar to the initial predicted medical profile of the first patient at the future time at which the first patient has the second age a2;

adding, to the predicted future medical profile for the first patient, one or more non-matching characteristics that each occur in at least one respective medical history of a respective nearest neighbor of the plurality of nearest neighbors but that does not occur in the medical history of the first patient;

generating a respective score for each of the one or more non-matching characteristics that each occur in at least one respective medical history of a respective nearest neighbor of the plurality of nearest neighbors but that does not occur in the medical history of the first patient, wherein the score for each non-matching characteristic represents a measure of how frequently the non-matching characteristic occurs in the medical histories of the plurality of nearest neighbors;

generating a presentation of the future medical profile for the first patient, the presentation including data representing a range of predicted outcomes for each of the one or more non-matching characteristics and a respective score for each of the one or more non-matching characteristics; and providing the presentation of the future medical profile for the first patient for display on a display device to the user.

16. The computer storage medium of claim 15, wherein:
generating the respective score for each of a plurality of non-matching characteristics comprises determining, by the one or more computers for each of the non-matching characteristics, a probability of the non-matching characteristic occurring to the first patient at the age N.

17. The computer storage medium of claim 16, the operations comprising:
determining one or more potential preventative measures for one of the non-matching characteristics that does not occur in the current medical history of the first patient; and
presenting, by the one or more computers, data for one or more potential preventative measures, an indication of the one of the non-matching characteristics, and the corresponding probability of the one of the non-matching characteristics occurring to the first patient.

18. The computer storage medium of claim 16, wherein determining the probability of the non-matching characteristics occurring to the first patient at the age N comprises:
determining, for each nearest neighbor having at least one of the non-matching characteristics, a respective similarity score that represents a degree of similarity between the corresponding nearest neighbor and the first patient; and
aggregating, for each of the non-matching characteristics, the similarity scores to determine the probability of the non-matching characteristic occurring to the first patient at the age N.

19. The computer storage medium of claim 18, wherein determining, for each nearest neighbor having at least one of the non-matching characteristics, the respective similarity score that represents the degree of similarity between the corresponding nearest neighbor and the first patient comprises:
determining a ratio of i) a first quantity of matching characteristics that occur in both the respective predicted medical profile of the corresponding nearest neighbor and the current medical history of the first patient to ii) a second quantity of non-matching characteristics that occur in the respective predicted medical profile of the corresponding nearest neighbor but that do not occur in the current medical history of the first patient; and
determining the respective similarity score using the corresponding ratio.

20. The computer storage medium of claim 15, the operations comprising:
determining, by the one or more computers and for each of the nearest neighbors, a respective second medical history; and
determining an estimated future healthcare value for the first patient using the predicted medical profiles and the second medical histories for the nearest neighbors.

21. The computer storage medium of claim 20, wherein:
determining the estimated future healthcare value for the first patient using the predicted medical profiles and the second medical histories for the nearest neighbors comprises determining, for each year from the first age of the first patient to the age N of the first patient, an estimated healthcare value.

22. The computer storage medium of claim 20, the operations comprising:
computing the plurality of nearest neighbors comprises computing the plurality of nearest neighbors for which at least a threshold quantity of characteristics occur in both the second medical history of the corresponding nearest neighbor and in the current medical history of the first patient for a predetermined age range of the nearest neighbors and the first patient.

23. The computer storage medium of claim 22, wherein the predetermined age range is from a younger age to the first age, and the younger age comprises an age three to five years younger than the first age.

24. The computer storage medium of claim 20, the operations comprising:
determining a current set of characteristics for the first patient at the first age from the current medical history;
determining, for each second medical history of one of the nearest neighbors, a set of characteristics for the respective nearest neighbor at the first age; and
determining that each characteristic in at least a threshold portion of characteristics from each of the sets of characteristics matches a corresponding characteristics in the current set of characteristics for the first patient.

25. The computer storage medium of claim 20, wherein the operations further comprise generating a ranking of the non-matching characteristics using a weighted average of probabilities of the characteristics occurring to the first patient.

26. The computer storage medium of claim 20, wherein the operations further comprise generating a ranking of the non-matching characteristics using an aggregation of a) at least a portion of each of a plurality of second medical histories, each second medical history for a respective nearest neighbor, and b) at least a portion of the predicted medical profiles for one or more of the nearest neighbors.

27. The computer storage medium of claim 15, wherein the current characteristics of the current medical history comprise one or more of biological statistics for the first patient, a medical diagnosis of the first patient, a record of a medical procedure performed on the first patient, a characterization of a hospital visit of the first patient, a record of a medication for the first patient, or a family history of the first patient.

28. The computer storage medium of claim 15, the operations comprising:
generating a second predicted medical profile of the first patient that includes an aggregation of at least a portion of the predicted medical profiles for the nearest neighbors.

29. A system comprising:
one or more computers; and
a non-transitory computer storage medium storing instructions that, when executed by the one or more computers, cause the one or more computers to perform operations comprising:
receiving, from a user, a request to compute a predicted future medical profile for a first patient having a future age N that is at least M*2 years beyond an initial age a1 using only M years of data, wherein the future medical profile assigns a score to each of a plurality of characteristics, each score for each characteristic representing a respective likelihood of the first patient having the respective characteristic at the future age N;
obtaining, by at least one of the computers, a current medical history of the first patient, the current medical history comprising data representing a plurality of current characteristics of a first patient having an initial age a1, a1 being less than N;
determining, using the current medical history of the first patient, an initial predicted medical profile of the first patient at a future time when the first patient will have a second age a2, wherein the second age a2 is no more than M years beyond the initial age a1;

obtaining M years of medical history for a plurality of other patients starting at a respective time when each of the other patients has a respective age that is at least the second age a2 and covering a respective time at which each of the other patients has attained the age N, wherein each medical history of each of the other patients indicates a respective age at which a particular characteristic occurred for the other patient;

computing a plurality of nearest neighbors to the first patient, each nearest neighbor having respective characteristics occurring at the second age a2 that are most similar to the initial predicted medical profile of the first patient at the future time at which the first patient has the second age a2;

adding, to the predicted future medical profile for the first patient, one or more non-matching characteristics that each occur in at least one respective medical history of a respective nearest neighbor of the plurality of nearest neighbors but that does not occur in the medical history of the first patient;

generating a respective score for each of the one or more non-matching characteristics that each occur in at least one respective medical history of a respective nearest neighbor of the plurality of nearest neighbors but that does not occur in the medical history of the first patient, wherein the score for each non-matching characteristic represents a measure of how frequently the non-matching characteristic occurs in the medical histories of the plurality of nearest neighbors;

generating a presentation of the future medical profile for the first patient, the presentation including data representing a range of predicted outcomes for each of the one or more non-matching characteristics and a respective score for each of the one or more non-matching characteristics; and providing the presentation of the future medical profile for the first patient for display on a display device to the user.

30. The system of claim 29, wherein:
generating the respective score for each of a plurality of non-matching characteristics comprises determining, by the one or more computers for each of the non-matching characteristics, a probability of the non-matching characteristic occurring to the first patient at the age N.

31. The system of claim 30, the operations comprising:
determining one or more potential preventative measures for one of the non-matching characteristics that does not occur in the current medical history of the first patient; and
presenting, by the one or more computers, data for one or more potential preventative measures, an indication of the one of the non-matching characteristics, and the corresponding probability of the one of the non-matching characteristics occurring to the first patient.

32. The system of claim 30, wherein determining the probability of the non-matching characteristics occurring to the first patient at the age N comprises:
determining, for each nearest neighbor having at least one of the non-matching characteristics, a respective similarity score that represents a degree of similarity between the corresponding nearest neighbor and the first patient; and
aggregating, for each of the non-matching characteristics, the similarity scores to determine the probability of the non-matching characteristic occurring to the first patient at the age N.

33. The system of claim 32, wherein determining, for each nearest neighbor having at least one of the non-matching characteristics, the respective similarity score that represents the degree of similarity between the corresponding nearest neighbor and the first patient comprises:
determining a ratio of i) a first quantity of matching characteristics that occur in both the respective predicted medical profile of the corresponding nearest neighbor and the current medical history of the first patient to ii) a second quantity of non-matching characteristics that occur in the respective predicted medical profile of the corresponding nearest neighbor but that do not occur in the current medical history of the first patient; and
determining the respective similarity score using the corresponding ratio.

34. The system of claim 29, the operations comprising:
determining, by the one or more computers and for each of the nearest neighbors, a respective second medical history; and
determining an estimated future healthcare value for the first patient using the predicted medical profiles and the second medical histories for the nearest neighbors.

35. The system of claim 34, wherein:
determining the estimated future healthcare value for the first patient using the predicted medical profiles and the second medical histories for the nearest neighbors comprises determining, for each year from the first age of the first patient to the age N of the first patient, an estimated healthcare value.

36. The system of claim 34, the operations comprising:
computing the plurality of nearest neighbors comprises computing the plurality of nearest neighbors for which at least a threshold quantity of characteristics occur in both the second medical history of the corresponding nearest neighbor and in the current medical history of the first patient for a predetermined age range of the nearest neighbors and the first patient.

37. The system of claim 36, wherein the predetermined age range is from a younger age to the first age, and the younger age comprises an age three to five years younger than the first age.

38. The system of claim 34, the operations comprising:
determining a current set of characteristics for the first patient at the first age from the current medical history;
determining, for each second medical history of one of the nearest neighbors, a set of characteristics for the respective nearest neighbor at the first age; and
determining that each characteristic in at least a threshold portion of characteristics from each of the sets of characteristics matches a corresponding characteristics in the current set of characteristics for the first patient.

39. The system of claim 34, wherein the operations further comprise generating a ranking of the non-matching characteristics using a weighted average of probabilities of the characteristics occurring to the first patient.

40. The system of claim 34, wherein the operations further comprise generating a ranking of the non-matching characteristics using an aggregation of a) at least a portion of each of a plurality of second medical histories, each second medical history for a respective nearest neighbor, and b) at least a portion of the predicted medical profiles for one or more of the nearest neighbors.

41. The system of claim 29, wherein the current characteristics of the current medical history comprise one or more of biological statistics for the first patient, a medical diagnosis of the first patient, a record of a medical procedure performed on the first patient, a characterization of a hospital visit of the first patient, a record of a medication for the first patient, or a family history of the first patient.

42. The system of claim 29, the operations comprising:
 generating a second predicted medical profile of the first patient that includes an aggregation of at least a portion of the predicted medical profiles for the nearest neighbors.

43. The method of claim 1, wherein the age N is ten or more years greater than the first age.

\* \* \* \* \*